United States Patent
Lange De Oliveira et al.

(10) Patent No.: US 9,339,802 B2
(45) Date of Patent: May 17, 2016

(54) ZINC CONTAINING METHANE AROMATIZATION CATALYST, METHOD OF MAKING A METHOD OF USING THE CATALYST

(75) Inventors: Armin Lange De Oliveira, Heidelberg (DE); Larry Lanier Marshall, Houston, TX (US); Peter Tanev Tanev, Katy, TX (US)

(73) Assignee: Shell Oil Company, Houston, TX (US)

( * ) Notice: Subject to any disclaimer, the term of this patent is extended or adjusted under 35 U.S.C. 154(b) by 319 days.

(21) Appl. No.: 13/981,342

(22) PCT Filed: Jan. 24, 2012

(86) PCT No.: PCT/US2012/022371
§ 371 (c)(1),
(2), (4) Date: Nov. 21, 2013

(87) PCT Pub. No.: WO2012/103095
PCT Pub. Date: Aug. 2, 2012

(65) Prior Publication Data
US 2014/0073828 A1    Mar. 13, 2014

Related U.S. Application Data

(60) Provisional application No. 61/436,238, filed on Jan. 26, 2011.

(51) Int. Cl.
*B01J 23/06* (2006.01)
*B01J 23/28* (2006.01)
(Continued)

(52) U.S. Cl.
CPC ............... *B01J 29/48* (2013.01); *B01J 29/405* (2013.01); *B01J 37/0203* (2013.01);
(Continued)

(58) Field of Classification Search
CPC ............ B01J 23/06; B01J 23/28; B01J 29/40; B01J 29/48; B01J 37/00; B01J 37/0203; B01J 37/08; B01J 37/12; C07C 2/76; C07C 2529/40; C07C 2529/48
USPC ..................... 502/71, 307, 321; 423/DIG. 22; 585/400, 417, 418
See application file for complete search history.

(56) References Cited

U.S. PATENT DOCUMENTS 6,239,057 B1    5/2001  Ichikawa et al.
8,742,189 B2 *  6/2014  Kiesslich ................. B01J 29/48
                                                          502/60
(Continued)

FOREIGN PATENT DOCUMENTS

CN    101687184    3/2010
WO    2009091336   7/2009
(Continued)

OTHER PUBLICATIONS

Wang, et al.; "Dehydrogenation and aromatization of methane under non-oxidizing conditions"; Catalysis Letters; vol. 21; pp. 35-41; 1993.
(Continued)

*Primary Examiner* — Patricia L Hailey

(57) ABSTRACT

A catalyst for converting methane to aromatic hydrocarbons is described herein. The catalyst comprises an active metal or a compound thereof, zinc or a compound thereof and an inorganic oxide support wherein the active metal is added to the support as a metal oxalate. A method of making the catalyst and a method of using the catalyst are also described.

24 Claims, 6 Drawing Sheets

(51) Int. Cl.
*B01J 29/40* (2006.01)
*B01J 37/00* (2006.01)
*B01J 37/12* (2006.01)
*B01J 29/48* (2006.01)
*B01J 37/02* (2006.01)
*B01J 37/32* (2006.01)
*C07C 2/76* (2006.01)

(52) U.S. Cl.
CPC ............ *B01J 37/0213* (2013.01); *B01J 37/32* (2013.01); *C07C 2/76* (2013.01); *B01J 2229/18* (2013.01); *C07C 2529/40* (2013.01); *C07C 2529/48* (2013.01); *Y02P 20/52* (2015.11); *Y02P 20/588* (2015.11)

(56) References Cited

U.S. PATENT DOCUMENTS

| | | | |
|---|---|---|---|
| 9,079,169 B2 * | 7/2015 | Tanev | B01J 23/28 |
| 2010/0285948 A1 | 11/2010 | Liu et al. | |
| 2011/0060176 A1 * | 3/2011 | Kiesslich | B01J 29/076 585/407 |
| 2011/0124933 A1 * | 5/2011 | Kiesslich | B01J 29/48 585/417 |
| 2012/0123176 A1 * | 5/2012 | Tanev | B01J 23/28 585/417 |

FOREIGN PATENT DOCUMENTS

| | | |
|---|---|---|
| WO | 2009124960 | 10/2009 |
| WO | 2010092851 | 8/2010 |
| WO | 2011143303 | 11/2011 |
| WO | 2012002269 | 1/2012 |

OTHER PUBLICATIONS

Guo, J., et al.; "Energy-Efficient coaromatization of methane and propane"; Journal of Natural Gas Chemistry; vol. 18, No. 3; pp. 260-272; Sep. 1, 2009.

Ichikawa, et al.; "Pressurized Dehydrocondensation of Methan Toward Benzene and Naphthalene on Mo/HZSM-5 Catalyst: Optimization of Reaction Parameters and Promotion by CO2 Addition"; Journal of Catalysis; vol. 206; pp. 134-142; 2002.

Bao, et al.; "On the Induction Period of Methane Aromatization Over Mo-Based Catalysts"; Journal of Catalysis; vol. 194; pp. 105-114; 2000.

Kinage, et al.; "Marked Enhancement of the Methane Dehydrocondensation Toward Benzene Using Effective Pd Catalytic Membrane Reactor with Mo/ZSM-5"; Catalysis Letters; vol. 88, Nos. 3-4; pp. 199-202; Jun. 2003.

Li, et al.; "Structure and Acidity of Mo/ZSM-5 Synthesized by Solid State Reaction for Methane Dehydrogenation and Aromatization"; Microporous and Mesoporous Materials; vol. 88; pp. 244-253; 2006.

* cited by examiner

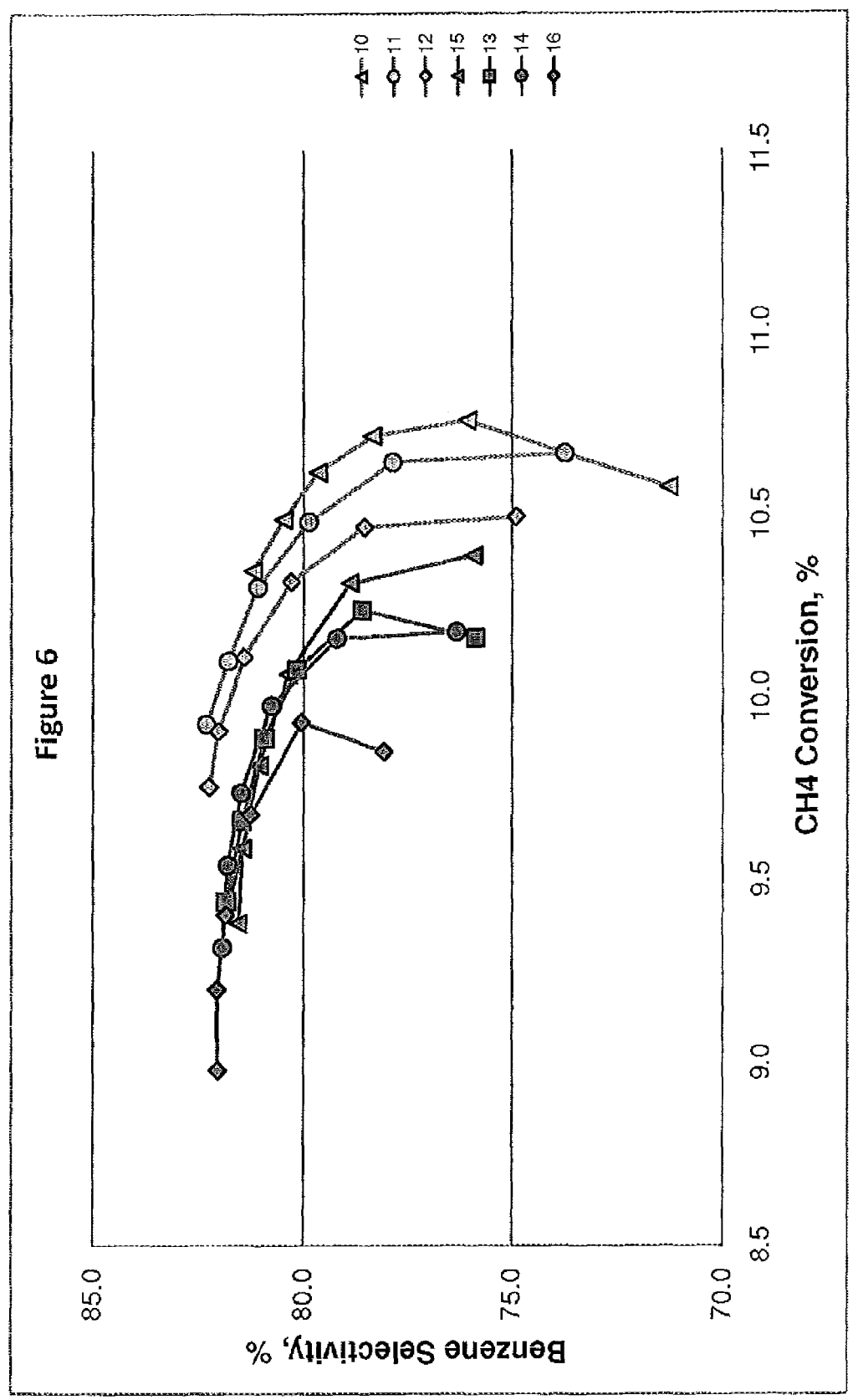

ated catalyst and process technology. Since then, many catalyst formulations have been prepared and tested and various reactor and process conditions and schemes have been explored.

ZINC CONTAINING METHANE AROMATIZATION CATALYST, METHOD OF MAKING A METHOD OF USING THE CATALYST

PRIORITY CLAIM

The present application claims priority from PCT/US2012/022371, filed 24 Jan. 2012, which claims priority from U.S. provisional 61/436,238, filed 26 Jan. 2011, which is incorporated herein by reference.

FIELD

This invention relates to a zinc-containing catalyst useful in converting methane to aromatic hydrocarbons, a method of making the catalyst and a method of using the catalyst to convert methane to aromatic hydrocarbons.

BACKGROUND

The aromatic hydrocarbons (specifically benzene, toluene and xylenes), are the main high-octane bearing components of the gasoline pool and important petrochemicals used as building blocks to produce high value chemicals and a variety of consumer products, for example, styrene, phenol, polymers, plastics, medicines, and others. Aromatics are primarily produced from oil-derived refinery feedstocks in such processes as catalytic reforming and cracking of heavy naphthas. However, the recent severe oil shortages and price spikes resulted in severe aromatics shortages and price spikes. Therefore, there is a need to develop new commercial routes to produce high value aromatics from highly abundant and cheap hydrocarbon feedstocks such as methane or stranded natural gas (which typically contains about 80-90% methane).

There are enormous proven stranded natural gas reserves around the world. According to some estimates, the natural gas reserves are at least equal to those of oil. However, unlike the oil reserves which are primarily concentrated in a few oil-rich countries and are properly and extensively exploited, upgraded and monetized, the natural gas reserves are much more broadly distributed around the world and significantly underutilized. Many developing countries that have significant natural gas reserves lack the proper infrastructure to exploit them and convert them to higher value products. Quite often, in such situations, natural gas is flared to the atmosphere and wasted. There is enormous economic incentive to develop new technologies that can efficiently convert methane or natural gas to higher value chemical products, specifically aromatics.

In 1993 Wang et al., (*Catal. Lett.* 1993, 21, 35-41), discovered that methane can be partially converted to benzene at atmospheric pressure and a temperature of 700° C. over a catalyst containing 2.0% wt molybdenum deposited on H-ZSM-5 zeolite support. Significantly, a low methane conversion of less than 10% but very high benzene selectivity of 100% was observed in these experiments. Subsequently, other researchers repeated the above work and found that Wang et al. did not quite identify all reaction products (naphthalene and others) and that when that is done the benzene selectivity falls in the range of 60-70%. These other researchers also pointed out that, the catalyst cokes up and deactivates very fast—as shown by complete loss of activity after about 4-5 hrs on stream. Since Wang's discovery, many academic and industrial research groups began working in this area and contributed to further developing various aspects of the methane to benzene catalyst and process technology. Since then, many catalyst formulations have been prepared and tested and various reactor and process conditions and schemes have been explored.

Despite these efforts and multimillion dollar annual R&D budgets, there is still no commercial methane aromatization or methane to benzene catalyst and process. The vast majority of researchers agree that the main obstacles to developing and commercializing efficient, direct methane to benzene process are the low methane conversion (still remaining at around 7-10%) and rapid coke formation, deposition and catalyst deactivation.

Therefore, there is a need to develop new methane aromatization catalysts that provide higher methane conversion at equal or higher selectivity to benzene relative to the prior art. Also, there is a need to develop catalysts that exhibit lower coking and deactivation rates, or exhibit improved stability relative to the catalysts of prior art.

SUMMARY OF THE INVENTION

The invention provides methane aromatization catalyst comprising an active metal or a compound thereof, zinc or a compound thereof and an inorganic oxide support wherein the active metal is added to the support as a metal oxalate and the active metal is not zinc.

The invention further provides a process for preparing a methane aromatization catalyst comprising: contacting an active metal oxalate with an inorganic oxide support to form a mixture, contacting zinc or a compound thereof with the mixture to form a catalyst precursor and calcining the precursor wherein the active metal oxalate does not comprise zinc.

The invention still further provides a process for producing aromatic hydrocarbons comprising contacting a gas stream comprising methane with a catalyst comprising molybdenum and zinc wherein the catalyst was prepared by contacting a molybdenum oxalate and a zinc compound with a zeolite-containing support.

BRIEF DESCRIPTION OF DRAWINGS

FIG. 6 shows the benzene selectivity versus methane conversion data obtained for the regenerated catalysts described in Examples 10-16.

DETAILED DESCRIPTION

Figure 1:
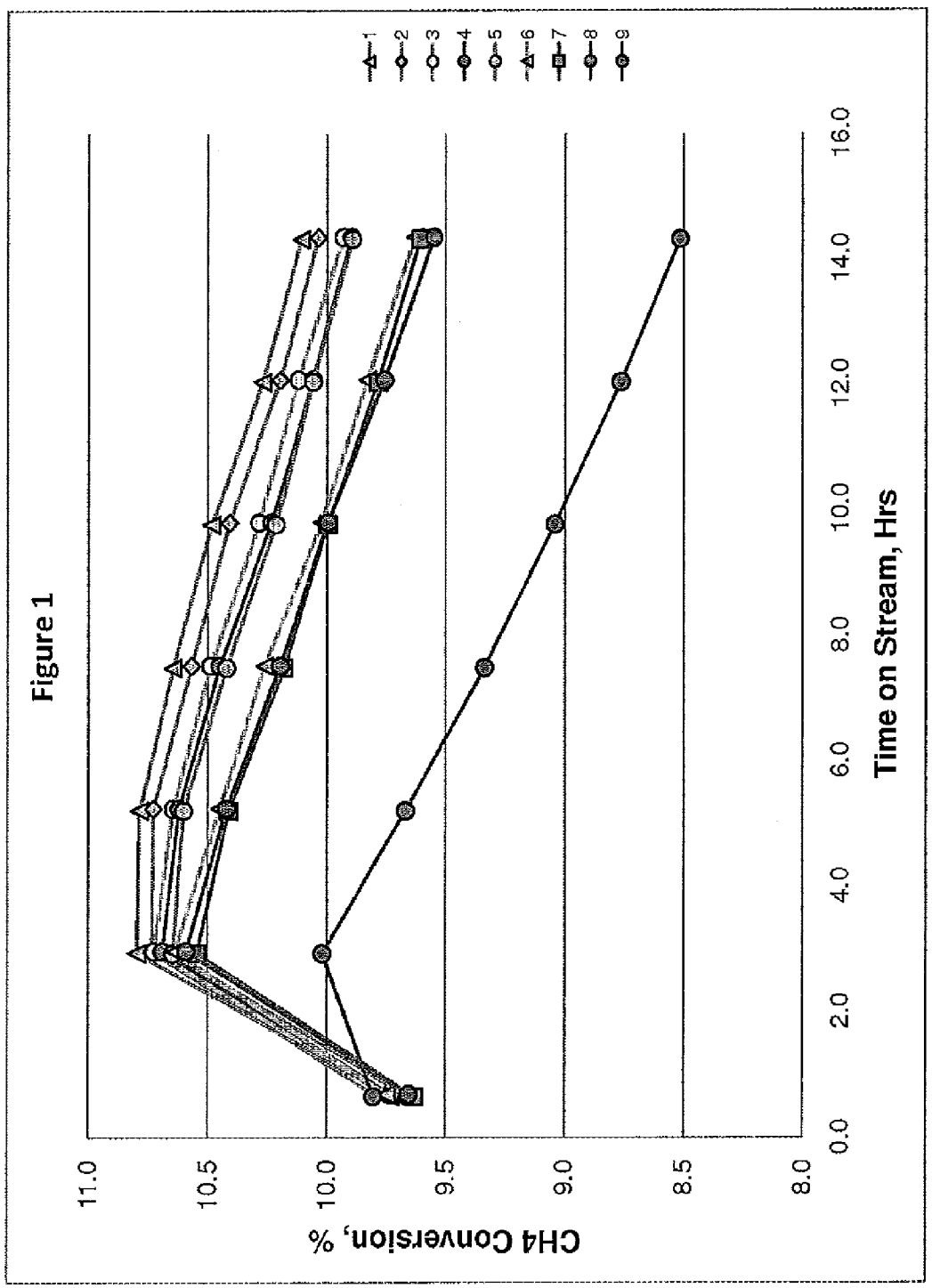
FIG. 1 shows the methane conversion versus time on stream data obtained for the catalysts described in Examples 1-9.

The methane aromatization catalyst described here comprises an active metal, a promoter and an inorganic oxide support. The active metal may be any metal, other than zinc, that exhibits catalytic activity when contacted with a gas stream comprising methane under methane aromatization conditions. The active metal may be selected from the group consisting of: vanadium, chromium, manganese, iron, cobalt, nickel, copper, gallium, germanium, niobium, molybdenum, ruthenium, rhodium, silver, tantalum, tungsten, rhenium, platinum and lead and mixtures thereof. The active metal is preferably molybdenum.

The promoter could be any element except the active metal that, when added in certain preferred amount and by certain preferred method of addition during catalyst synthesis, improves the performance of the catalyst in the methane aromatization reaction. The preferred promoter is zinc. The promoter may be deposited from zinc precursors or precursor solutions comprising zinc nitrate, zinc chloride, zinc oxychloride, zinc acetate, zinc acetylacetonate, zinc alkoxide, zinc oxide, and zinc oxalate. Preferably, the zinc precursor is selected from the group of zinc nitrate, zinc oxide or zinc oxalate.

The inorganic oxide support can be any support that, when combined with the active metal and the promoter contributes significantly to the overall catalyst performance exhibited in the methane aromatization reaction. The support is suitable for treating or impregnating with the active metal compound or solution thereof and zinc promoter compound or solution thereof. The inorganic support preferably has a well developed porous structure with sufficiently high surface area and pore volume and suitable surface acidity. The inorganic oxide support may be selected from the group consisting of: zeolites, non-zeolitic molecular sieves, silica, alumina, zirconia, titania, yttria, ceria, rare earth metal oxides and mixtures thereof. The inorganic oxide support of this invention contains zeolite as the primary component. The zeolite is selected from the group of ZSM-5, ZSM-22, ZSM-8, ZSM-11, ZSM-12 or ZSM-35 zeolite structure types. The zeolite is preferably a ZSM-5 zeolite. The ZSM-5 zeolite further may have a $SiO_2/Al_2O_3$ ratio of 10 to 100. Preferably, the $SiO_2/Al_2O_3$ ratio of the zeolite is in the range of 20-50. Even more preferably the $SiO_2/Al_2O_3$ ratio is from 20 to 40 and most preferably about 30. The zeolite support may further contain about 15-30% wt of a binder that allows for shaping of the catalyst in the desired form for achieving the desired high catalyst mechanical strength for commercial operation. The binder is selected from the group of silica, alumina, zirconia, titania, yttria, ceria, rare earth oxides or mixtures thereof.

The active metal or compound thereof is added to the support in the form of a metal oxalate precursor. If the metal oxalate is not commercially available, the active metal or compound thereof is reacted with oxalic acid to form the desired metal oxalate. The metal oxalate precursor can be formed by adding the necessary amount of metal oxide powder to a solution of oxalic acid. Preferably, the metal oxide powder is $Mo(VI)O_3$. The mixture may be stirred and/or heated as necessary to obtain a clear solution of the metal oxalate.

The zinc promoter may be added to the zeolite-containing support as a zinc compound or as a zinc compound solution. In a preferred preparation, the zinc compound solution is added first to the support via an impregnation. The support is then dried and calcined. Next, the metal oxalate solution is impregnated on the zinc-containing support and the impregnate is dried and calcined to form the finished zinc-containing methane aromatization catalyst of this invention. Yet, in another preferred preparation, the zinc compound is directly added to or added in the form of a clear solution to the active metal oxalate solution to form an active metal and zinc oxalate-containing impregnating solution. This solution is then used to impregnate the zeolite containing support. The impregnated support is then again dried and calcined to form the finished active metal, zinc and zeolite comprising methane aromatization catalyst of this invention.

The inorganic oxide support can be mixed with the active metal oxalate and a suitable zinc compound or with active metal oxalate and zinc oxalate to afford a solid state mixture that can then be subjected to calcination in an oven under dry air flow atmosphere to evaporate and deposit the active metal and zinc in the pores of the zeolite. This technique is known to those skilled in the art as solid state ion-exchange. In a more preferred embodiment, the inorganic support is impregnated first with a solution of zinc compound and then with a metal oxalate solution. Yet in another preferred embodiment, a zinc compound or a solution thereof are added to the active metal oxalate solution to form a zinc and active metal oxalate impregnating solution and then the solution is used to impregnate the support. The support is left in contact with the solution for a sufficient period of time to allow the solution to penetrate the pores of the support and for the zinc and molybdenum to react with the active centers of the zeolite-containing support Other components or promoters can be added to the support in various precursor forms and impregnation order to improve various aspects of the finished catalyst physical or mechanical properties or catalytic performance. For example, the promoter precursor could be added to the support in a mixing or impregnation step before, after or simultaneously with the active metal oxalate.

The impregnated support is then dried and calcined to form the finished catalyst. The drying and calcination steps typically include flowing dry air or nitrogen in a volume of from 1 to 60 liters per hour over the catalyst precursor, preferably from 20 to 50 liters per hour. The impregnated support may be subjected to a series of specific heating rates and temperature ramps to complete the cross-linking of the structure and to form the finished active metal, zinc and zeolite comprising methane aromatization catalyst.

The impregnated support is preferably dried and calcined by heating it at a temperature of from 80° C. to 120° C. for a period of time of at least 20 minutes, preferably of from 60 minutes to 180 minutes. The temperature is then increased to from 275° C. to 325° C. at a rate of from 1° C. to 10° C. per minute, preferably from 2 to 4° C. per minute. That temperature is then maintained for a period of time of at least 20 minutes, preferably from 60 minutes to 180 minutes. Then the temperature is increased again, this time to from 475° C. to 525° C. at a rate of 1° C. to 10° C. per minute, preferably 2 to 4° C. per minute. This temperature is then maintained for at least 20 minutes, preferably from 20 minutes to 240 minutes, and even more preferably of from 120 minutes to 240 minutes.

The catalyst formed by the above steps is then preferably cooled to a temperature in the range of from 80° C. to 120° C.

The zinc-containing methane aromatization catalyst is useful in the reaction of methane or methane-containing gases, for example, natural gas, to form aromatic hydrocarbons. Natural gas is defined as a mixture of saturated hydrocarbons having a carbon number of from 1 to 5, preferably of from 1 to 4.

The conversion of methane-containing gas to aromatic hydrocarbons is typically carried out in a reactor comprising a catalyst which is active in the conversion of methane to aromatics. The methane-containing gas that is fed to the reactor comprises more than 50% vol. methane, preferably more than 75% vol. methane and more preferably of from 75% vol. to 100% vol. methane.

The conversion of methane-containing gas is carried out at a space velocity of from 100 to 10000 $h^{-1}$, a pressure of from 0.5 to 10 bar and a temperature or from 500 to 850° C. More preferably, the conversion is carried out at space velocity of from 300 to 3000 h$^{-1}$, a pressure of from 0.5 to 5 bar and a temperature of from 600 to 800° C. Even more preferably, the conversion is carried out at space velocity of from 500 to 1500 h$^{-1}$, a pressure of from 0.5 to 3 bar and a temperature of from 650 to 750° C. Various co-feeds such as CO, $CO_2$ or $H_2$ that react with the coke precursors or prevent their formation during methane conversion could be added at levels of <10% vol. to the methane-containing feed to improve the stability performance or regenerability of the catalyst. The methane conversion is then carried out until conversion falls to values that are lower than those that are economically acceptable. At this point, the zinc-containing catalyst of this invention has to be regenerated to restore its methane aromatization activity. Following the regeneration, the catalyst is again contacted with a methane-containing feed in a subsequent process cycle.

The catalyst regeneration can be performed by different techniques known to those skilled in the art that are effective at removing the carbonaceous deposits and restoring the catalyst activity. For this particular invention, the spent catalysts were regenerated by first cooling them from methane aromatization reaction temperature to 480° C. and then subjecting them to purging with argon at 1000 h$^{-1}$, atmospheric pressure and 480° C. for one hour. Next, the catalysts were subjected to 2000 h$^{-1}$ of 0.5 to 2.0% vol. $O_2/N_2$ gas flow at atmospheric pressure and 480° C. for 22 hrs to slowly burn off the coke from the surface of the catalyst and restore its methane aromatization activity.

EXAMPLES

The following examples were carried out to compare the catalytic performance of molybdenum and zinc-containing methane aromatization catalysts. The molybdenum precursor, preparation method of the catalyst and the loading level of the active metal, molybdenum, on the catalysts were varied in these examples.

To remove any performance differences caused by the inorganic oxide support, all catalysts as described in the examples were prepared using the same H-ZSM-5 zeolite support. The support was prepared by calcining a batch of commercially available Zeolyst International Company, CBV-3024E, $NH_4^+$/ZSM-5 zeolite powder with $SiO_2/Al_2O_3$ ratio of 30 under dry air at 500° C. for sufficient period of time to convert it from $NH_4^+$ into $H^+$ form.

The performance tests of all catalysts were conducted in the same manner. Prior to testing, the catalysts were loaded into the reactors as 2.5 cc charges and pretreated insitu by: (i) establishing 5 L/hr pure $H_2$ flow, at 1 bar and heating from ambient temperature to 240° C. at 0.5° C./min and holding at 240° C. for 4 hrs; (ii) heating under the same flow and pressure to 480° C. at 2° C./min and holding at 480° C. for 2 hrs and (iii) finally, heating under the same conditions to 700° C. at 2° C./min and holding for 1.5 hrs to complete the reduction. The catalysts were then purged with 2.5 L/hr of pure argon for 20 min and then contacted with a methane-containing feed comprising 90% vol. methane and 10% vol. argon at 1000 hr$^{-1}$ GHSV, 1 bar pressure and 700° C. The argon was used as an internal standard for the GC analysis.

Figure 2:
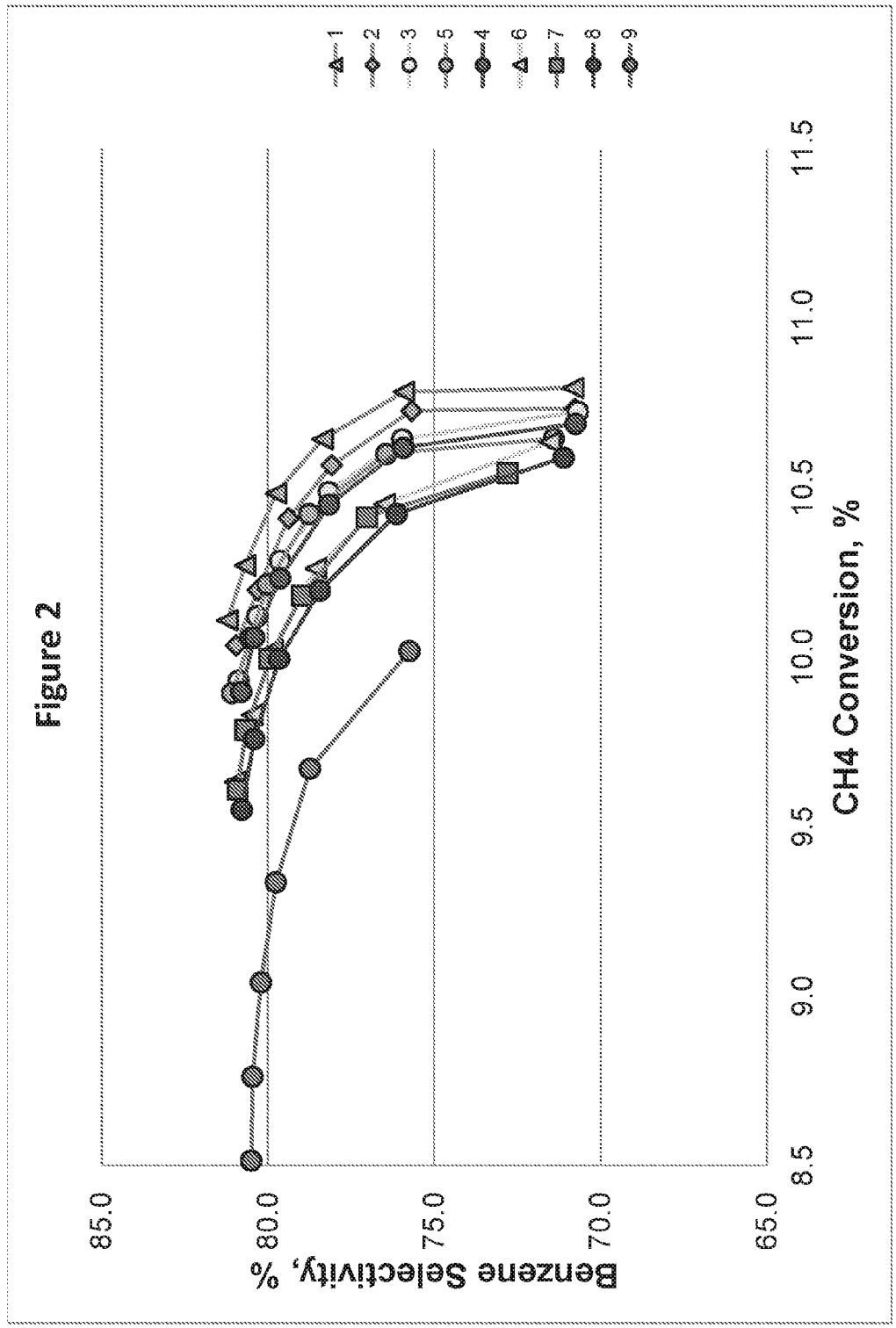
FIG. 2 shows the benzene selectivity versus methane conversion data obtained for the catalysts described in Examples 1-9.

During the tests, product samples were automatically withdrawn (each 20 min) from the reactors from a zone located directly under the catalyst bed and analyzed in a GC analyzer. FIG. 1 shows the $CH_4$ conversion versus time on stream test data obtained for several zinc-containing 6% wt Mo/H-ZSM-5 catalysts doped with different levels of zinc (Examples 1-9). FIG. 2 shows the corresponding benzene selectivity versus $CH_4$ conversion data for these catalyst formulations. The analysis of the data in the figures reveals that, the amount of zinc promoter has a very significant effect on the performance of the catalyst in the methane aromatization reaction. Obviously, the catalyst formulations promoted with about 0.7 and 1.0% wt Zn exhibited the highest $CH_4$ conversion, benzene selectivity and stability (sustained their performance better) among all Zn containing 6% wt Mo/H-ZSM-5 formulations.

Figure 3:
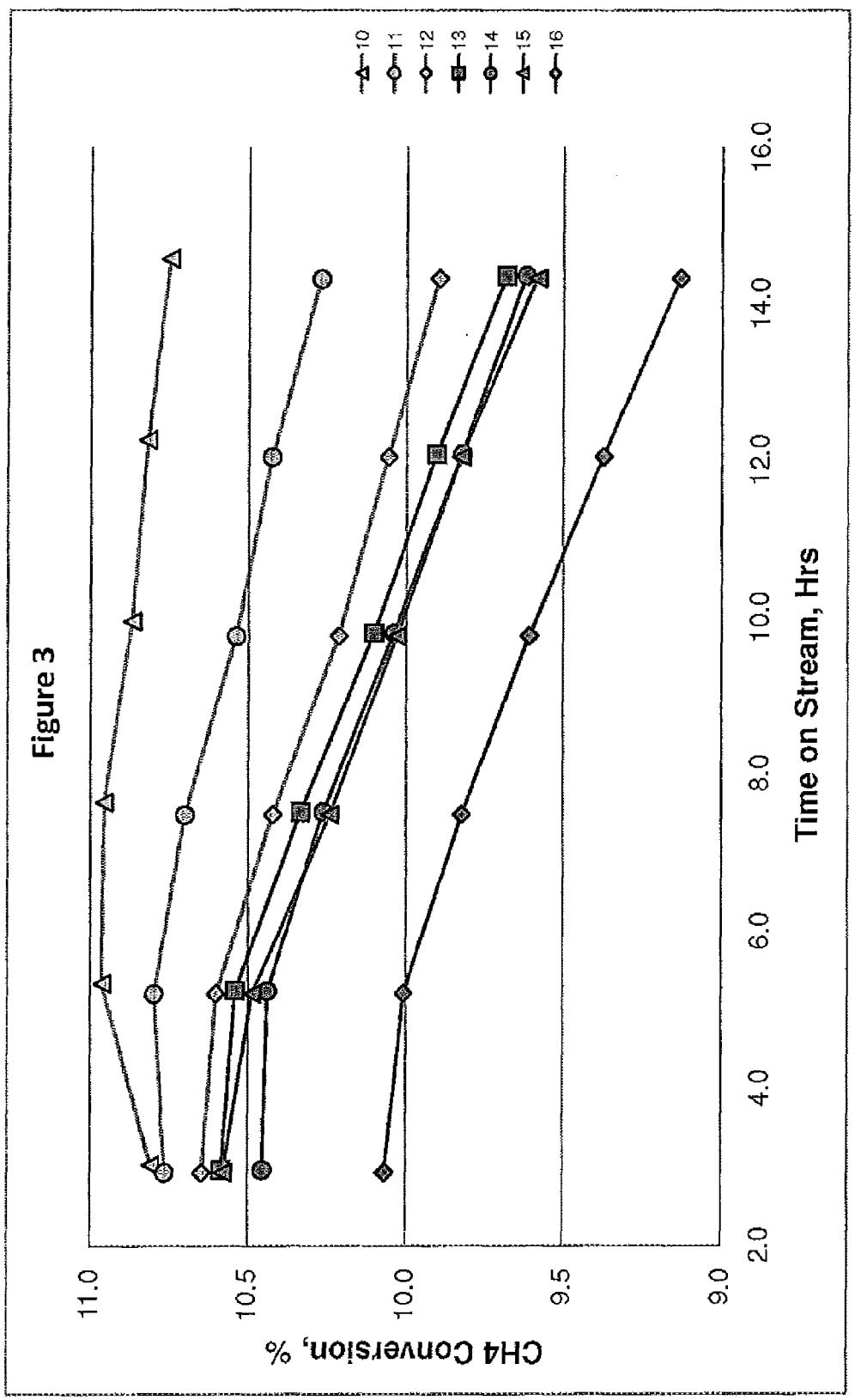
FIG. 3 shows the methane conversion versus time on stream data obtained for the catalysts described in Examples 10-16.
Figure 4:
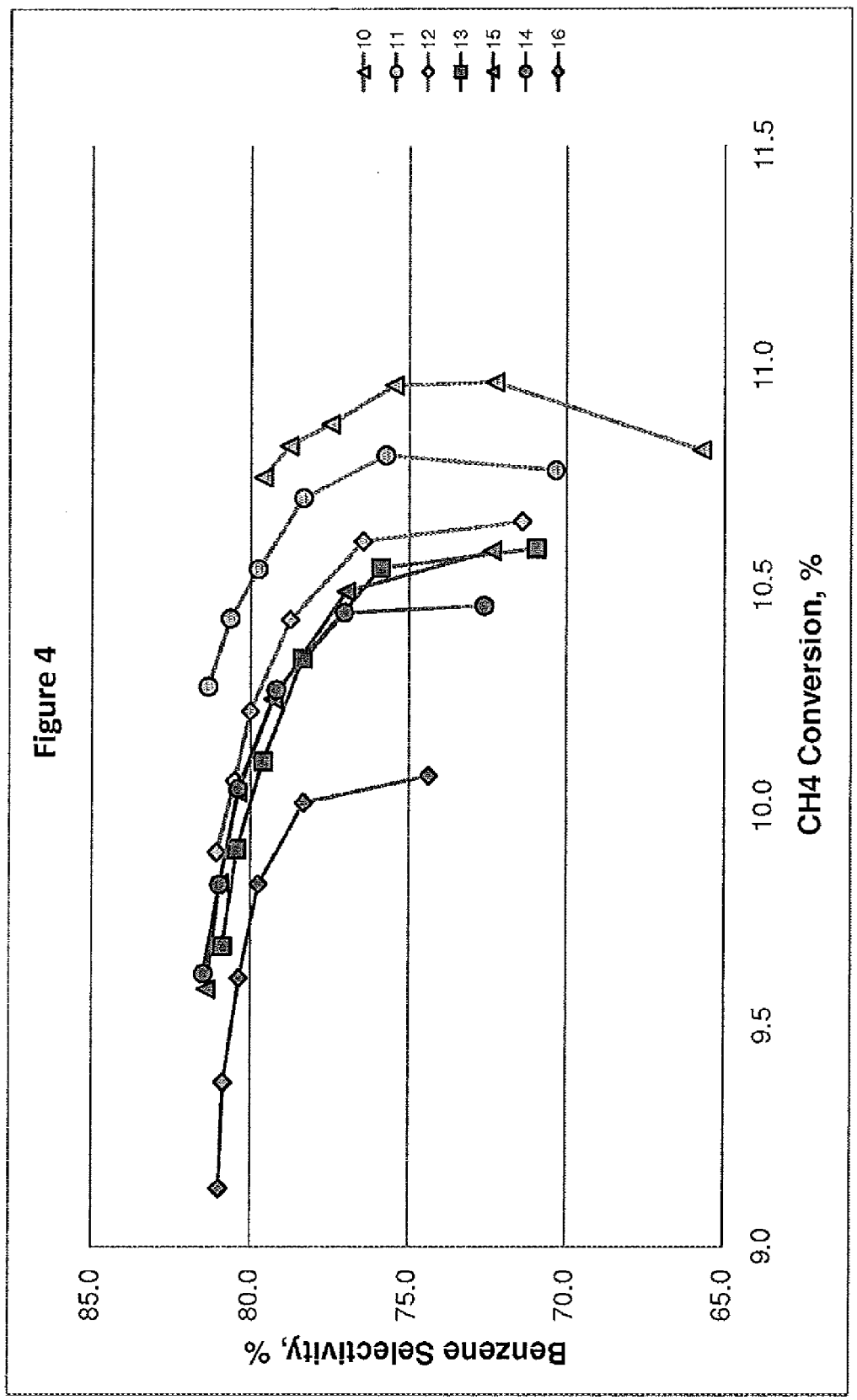
FIG. 4 shows the benzene selectivity versus methane conversion data obtained for the catalysts described in Examples 10-16.

FIGS. 3 and 4 show the $CH_4$ conversion vs. time on stream and benzene selectivity vs. $CH_4$ conversion test data, respectively, for 1.0% wt Zn-promoted 6% wt Mo/H-ZSM-5 formulations of this invention (Examples 10-12), prepared via different order of addition or impregnation methods (zinc impregnated prior to, simultaneously or following impregnation with molybdenum oxalate solution). For comparison, we have also added data obtained for several prior art 6% wt Mo/H-ZSM-5 formulations prepared from Mo oxalate and other Mo precursors (Examples 13-16). The comparison of the data clearly reveals that the 1.0% wt Zn promoted 6% wt Mo/H-ZSM-5 formulations of this invention exhibit significantly better $CH_4$ conversion, benzene selectivity and performance stability relative to the Mo-only containing formulations of the prior art. In addition, it is noteworthy that the addition of 1.0% wt Zn promoter prior to the Mo impregnation step (see sample 10) affords the best performance relative to the other 2 methods of Zn deposition.

Following the tests, the spent catalysts from Examples 10-16 were regenerated. The regeneration was done insitu by first cooling the catalysts to 480° C. and then subjecting them to purging with argon at 1000 h$^{-1}$, 1 atm and 480° C. for 1 hr. Next, the catalysts were subjected to 2000 h$^{-1}$ of 0.5 to 2.0% vol. $O_2/N_2$ gas flow, 1 atm and 480° C. for 22 hrs to slowly burn off the coke from the surface of the catalysts and restore their activity. The regenerated catalysts were then tested again.

Figure 5:
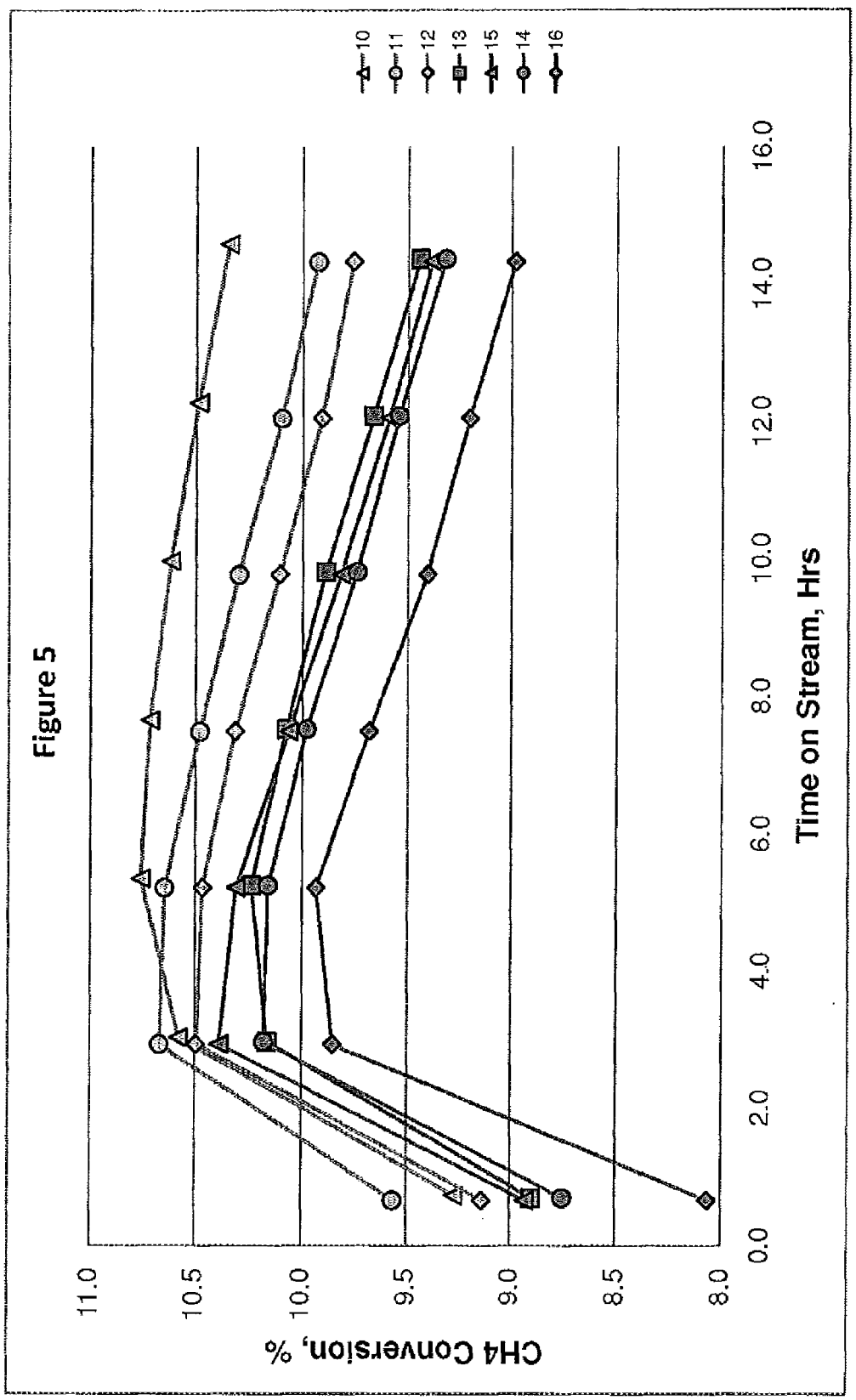
FIG. 5 shows the methane conversion versus time on stream data obtained for the regenerated catalysts described in Examples 10-16.

FIGS. 5 and 6 show the $CH_4$ conversion vs. time on stream and benzene selectivity vs. $CH_4$ conversion test data, respectively, for the regenerated samples (Examples 10-16) from the previous tests. The comparison of the data shows that, the magnitude of the performance advantage afforded by the 1.0% wt Zn-promoted 6.0% wt Mo/H-ZSM-5 catalysts of this invention over 6.0% wt Mo/H-ZSM-5 catalysts of the prior art is preserved following the regeneration (in the $2^{nd}$ cycle). This signifies that the performance advantage afforded by the zinc-promoted methane aromatization catalysts of this invention is sustained following a regeneration treatment.

The aforementioned catalysts were prepared as described in the following Examples.

Example 1

A molybdenum oxalate solution was prepared by dissolving 144.07 g of $MoO_3$ and 144.07 g of oxalic acid dihydrate (to give a molar ratio of molybdenum to oxalic acid=1:1.14) in a 1000 mL beaker filled with deionized water in such a way as to prepare a total of 500 mL of 2 mol/L molybdenum oxalate solution. The solution is then heated to 80° C. and stirred for 4 hrs or until complete dissolution of the molybdenum oxide and formation of molybdenum oxalate.

A zinc nitrate solution was prepared by mixing 30.35 g of $Zn(NO_3)_2 \times 6H_2O$ with water to make 50 mL of solution with a concentration of zinc of 2 mol/L.

Simultaneously, a sufficient quantity of $NH_4^+$-ZSM-5 zeolite powder was shaped by compacting it in a compactor at 180 bar (3 times recycle) and then sieved to obtain support particles fraction of from ~315-500 microns. The shaped NH4+ form zeolite support particles were then placed in an oven and calcined at a temperature of 500° C. for 4 hours to convert them to an H+ form.

Eight grams of the H+-ZSM-5 zeolite support particles were then impregnated with the molybdenum oxalate solution as follows. The impregnation was carried out in a Perkin Elmer MultiProbe II ex robotic pipetor that allows for automated simultaneous impregnation of several support samples. First, the impregnated support was weighed into a shallow bed dish and spread evenly to maximize impregnation surface. The dish was then placed in the Perkin Elmer Multiprobe in preparation for impregnation. Next, a 2.66 mL quantity of the above described molybdenum oxalate impregnation solution was mixed with 4.54 mL of deionized water and loaded in the pipetor. Then, the impregnation program was started and the robotic head gradually impregnated the support in the dish in reproducible manner.

The impregnated sample was then aged for 30 minutes; shock frozen by pouring liquid nitrogen over the sample and letting it dry for 24 hours. The sample is then air dried and calcined in a programmable oven by subjecting it to a 1 L/min flow of dry air and heating it to 300° C. at a rate of 1° C. per minute. The temperature was maintained for 2 hours. Then, the temperature was raised to 550° C. at a rate of 1° C. per minute and held for 2 hours. The calcined catalyst sample was then sieved to remove fines to obtain the desired 315-500 microns fraction.

Seven grams of the molybdenum impregnated and calcined support were then impregnated in a second step with a mixture containing 1.08 mL of zinc nitrate solution and 5.22 mL of deionized water. The impregnation was carried out as described above. The same steps of shock freezing, drying, calcining, and sieving were then carried out. The catalyst had a molybdenum content of 6.0% wt and a zinc content of 1.0% wt.

Example 2

The catalyst of this example was prepared in the same manner as the one in Example 1 except that the zeolite powder was shaped by compacting it in a compactor at 100 bar (6 times recycle) instead of 180 bar. The finished catalyst contained 6.0% wt of molybdenum and 1.0% wt of zinc.

Example 3

The catalyst of this Example was prepared in the same manner as the catalyst of Example 1 except that the zeolite powder was shaped by compacting it in a compactor at 250 bar (2 times recycle) and the impregnation was carried out in one step by impregnating the support with a mixture of 2.68 mL of the molybdenum oxalate solution, 0.46 mL of the zinc nitrate solution and 4.06 mL of deionized water. The finished catalyst had a molybdenum content of 6.0% wt and a zinc content of 0.7% wt.

Example 4

The catalyst of this example was prepared in the same manner as described in Example 3 except that the impregnating solution was prepared by mixing 2.68 mL of the molybdenum oxalate solution, 0.53 mL of zinc nitrate solution and 3.99 mL of deionized water. The finished catalyst had a molybdenum content of 6.0% wt and a zinc content of 0.8% wt.

Example 5

The catalyst of this example was prepared in the same manner as described in Example 3 except that the impregnating solution was prepared by mixing 2.69 mL of the molybdenum oxalate solution, 0.66 mL of the zinc nitrate solution and 3.85 mL of deionized water. The finished catalyst had a molybdenum content of 6.0% wt and a zinc content of 1.0% wt.

Example 6

The catalyst of this example was prepared in the same manner as described in Example 3 except that the impregnating solution was prepared by mixing 2.68 mL of the molybdenum oxalate solution, 0.33 mL of the zinc nitrate solution and 4.20 mL of deionized water. The finished catalyst had a molybdenum content of 6.0% wt and a zinc content of 0.5% wt.

Example 7

The catalyst of this example was prepared in the same manner as described in Example 3 except that the impregnating solution was prepared by mixing 2.71 mL of the molybdenum oxalate solution, 1.19 mL of the zinc nitrate solution and 3.29 mL of deionized water. The finished catalyst had a molybdenum content of 6.0% wt and a zinc content of 1.8% wt.

Example 8

The catalyst of this example was prepared in the same manner as described in Example 3 except that the impregnating solution was prepared by mixing 2.68 mL of the molybdenum oxalate solution, 0.39 mL of the zinc nitrate solution and 4.13 mL of deionized water. The finished catalyst had a molybdenum content of 6.0% wt and a zinc content of 0.6% wt.

Example 9

The catalyst of this Example was prepared in the same manner as the catalyst of Example 1 except that the zeolite powder was shaped by compacting it in a compactor at 250 bar, the impregnation mixtures were different, and there was no calcining step between the two impregnations. The support was first impregnated with a solution mixture containing 2.77 mL of the molybdenum oxalate solution and 4.43 mL of deionized water. The molybdenum impregnated support was shock frozen and dried for 24 hours. Then, the support was impregnated in a second step with a solution of 2.44 mL of the zinc nitrate solution and 4.76 mL of deionized water. The finished catalyst had a molybdenum content of 6.0% wt and a zinc content of 3.6% wt.

Example 10

The catalyst of this Example was prepared in the same manner as the catalyst of Example 1 with the following differences. The zeolite powder was shaped by compacting it in a compactor at 250 bar (with 3 times recycle) instead of at 100 bar. The impregnation mixtures were different and the impregnations were carried out in reverse order. In addition, the first impregnation was carried out using 60 g of support and a mixture of 4.63 mL of the zinc nitrate solution and 37.37 mL of deionized water. Following the impregnation, the support was shock frozen, dried and calcined as in Example 1. Then, 45 g of the zinc-impregnated support were subjected to second impregnation with a mixture containing 14.97 mL of the molybdenum oxalate solution and 16.53 mL of deionized water. The catalyst was then shock frozen, dried and calcined as in Example 1. The finished catalyst had a molybdenum content of 6.0% wt and a zinc content of 1.0% wt.

Example 11

The catalyst of this Example was prepared in a similar manner as in Example 10, albeit with less support. Eight grams of support were first impregnated with a mixture of 0.62 mL of the zinc nitrate solution and 6.58 mL of deionized water. The zinc-impregnated support was shock frozen, dried and calcined as in Example 10. Then 7 g of support was impregnated in a second step with 2.33 mL of the molybdenum oxalate and 3.97 mL of deionized water. The wet catalyst was then shock frozen, dried and calcined as in Example 10. The finished catalyst had a molybdenum content of 6.0% wt and a zinc content of 1.0% wt.

Example 12

The catalyst of this Example was prepared as described in Example 5. The finished catalyst had a molybdenum content of 6.0% wt and a zinc content of 1.0% wt.

Comparative Examples

Example 13

The catalyst of this Example was prepared as described in Example 3 except that the addition of zinc nitrate solution was omitted—the impregnation solution and finished catalyst did not contain zinc. Prior to impregnation, the support was flattened into the dish with a stamp to make for a more even impregnation surface. The support was impregnated with a mixture of 2.66 mL of the molybdenum oxalate solution and 4.54 mL of deionized water. The wet catalyst was then shock frozen, dried, calcined and sieved as described above. The finished catalyst had a molybdenum content of 6.0% wt.

Example 14

The catalyst of this Example was prepared as described in Example 13 except that the support was not flattened so the impregnation was carried out on an uneven support surface.

Example 15

The catalyst of this example was prepared in the same manner as described in Example 13 except that the impregnating solution was prepared by mixing 4.63 g of ammonium heptamolybdate with 25 mL of deionized water. Then, 5.07 mL of the above impregnation solution was mixed with 2.13 g of deionized water and this final solution was used to impregnate 8 g of the zeolite support. The wet catalyst was then shock frozen, dried, calcined and sieved. The catalyst was found to have a molybdenum content of 6.0% wt.

Example 16

This example describes a catalyst prepared by physical mixing or the so-called "solid state ion-exchange" method. The zeolite support was prepared following the same steps as described in the preceding examples. Then, 6.383 g of $MoO_3$ (in solid form) was mixed with 100 g of the zeolite support. The mixing was carried out in a grinder using ten separate portions of the above solid mix at a time. The physical mixture was then compacted in a Powtec compactor at a pressure force of 250 bar (with 3 times recycle). The obtained catalyst precursor was then dried, calcined and sieved as described in the preceding examples. The finished catalyst was found to have a molybdenum content of 4.081% wt (equivalent to 6% wt of $MoO_3$).

Table 1 provides a summary of the information presented herein with respect to the Examples. The columns for Mo added and Zn added indicate the order in which the metals were added to the zeolite. For Examples 3-8 and 12, the molybdenum and zinc were combined and then the zeolite was impregnated with the mixture.

TABLE 1

| Example | Mo added | Zn added | Mo content (% wt) | Zn content (% wt) |
|---|---|---|---|---|
| 1 | First | Second | 6.0 | 1.0 |
| 2 | First | Second | 6.0 | 1.0 |
| 3 | | Simultaneously | 6.0 | 0.7 |
| 4 | | Simultaneously | 6.0 | 0.8 |
| 5 | | Simultaneously | 6.0 | 1.0 |
| 6 | | Simultaneously | 6.0 | 0.5 |
| 7 | | Simultaneously | 6.0 | 1.8 |
| 8 | | Simultaneously | 6.0 | 0.6 |
| 9 | First | Second | 6.0 | 3.6 |
| 10 | Second | First | 6.0 | 1.0 |
| 11 | Second | First | 6.0 | 1.0 |
| 12 | | Simultaneously | 6.0 | 1.0 |
| 13 | First | N/A | 6.0 | 0.0 |
| 14 | First | N/A | 6.0 | 0.0 |
| 15 | First | N/A | 6.0 | 0.0 |
| 16 | First | N/A | 4.08 | 0.0 |

What is claimed is:

1. A methane aromatization catalyst comprising an active metal or a compound thereof, zinc or a compound thereof and an inorganic oxide support wherein the active metal is added to the support as a metal oxalate and the active metal is not zinc and wherein the active metal comprises molybdenum, wherein the molybdenum concentration in the catalyst is in the range of from 6 to 10% wt, and wherein the zinc is present in an amount of from 0.7 to 2.0% wt.

2. A catalyst as claimed in claim 1 wherein an additional promoter compound is added to the support.

3. A catalyst as claimed in claim 1 wherein the inorganic oxide support is a zeolite or zeolite-containing support.

4. A catalyst as claimed in claim 3 wherein the zeolite is a ZSM-5 type zeolite.

5. A catalyst as claimed in claim 1 wherein the zinc is added as a zinc oxalate.

6. A process for preparing a methane aromatization catalyst comprising: contacting an active metal oxalate with an inorganic oxide support to form a mixture, contacting zinc or a compound thereof with the mixture to form a catalyst precursor and calcining the precursor wherein the active metal oxalate does not comprise zinc and wherein the active metal comprises molybdenum, wherein the molybdenum concentration in the catalyst is in the range of from 6 to 10% wt, and wherein the zinc is present in an amount of from 0.7 to 2.0% wt, and wherein the active metal oxalate is in the form of a solution that is used to impregnate the inorganic support.

7. A process as claimed in claim 6 wherein the zinc is in the form of a solution that is used to impregnate the support.

8. A process as claimed in claim 6 wherein the active metal oxalate and zinc are combined and then contacted with the inorganic oxide support to form the catalyst precursor.

9. A process as claimed in claim 6 wherein the zinc or compound thereof is impregnated on the support and then the active metal oxalate is impregnated on the support.

10. A process as claimed in claim 6 wherein the zinc compound comprises zinc oxalate.

11. A process as claimed in claim 6 wherein the inorganic oxide support is a zeolite or zeolite-containing support.

12. A process as claimed in claim 6 wherein the support comprises ZSM-5 type zeolite.

13. A process as claimed in claim 6 wherein the support contains zeolite and a binder.

14. A process as claimed in claim 6 wherein contacting the metal oxalate with the inorganic oxide support is carried out at a temperature in the range of from 0° C. to 100° C.

15. A process as claimed in claim 6 wherein contacting the metal oxalate with the inorganic oxide support is carried out at a temperature in the range of from 15° C. to 40° C.

16. A process as claimed in claim 6 further comprising a drying step before the calcining.

17. A process as claimed in claim 16 wherein the drying and calcining comprises:
   a. subjecting the impregnated support to a temperature of from 70° C. to 120° C. for at least 20 minutes;
   b. increasing the temperature at a rate of from 1° C. to 10° C. per minute to a temperature of from 275° C. to 325° C.;
   c. maintaining the temperature achieved in step (b) for at least 20 min;
   d. increasing the temperature at a rate of from 1° C. to 30° C. per minute to a temperature of from 475° C. to 650° C.; and
   e. maintaining the temperature achieved in step (d) for at least 20 min.

18. A process as claimed in claim 16 wherein the drying and calcining comprises:
   a. subjecting the impregnated support to a temperature of from 70° C. to 120° C. for from 20 minutes to 240 minutes;
   b. increasing the temperature at a rate of from 1° C. to 10° C. per minute to a temperature of from 275° C. to 325° C.;
   c. maintaining the temperature achieved in step (b) for from 20 minutes to 240 minutes;
   d. increasing the temperature at a rate of from 1° C. to 30° C. per minute to a temperature of from 475° C. to 550° C.; and
   e. maintaining the temperature achieved in step (d) for from 20 minutes to 240 minutes.

19. A process as claimed in claim 6 further comprising cooling the impregnated support after calcination.

20. A process for producing aromatic hydrocarbons comprising contacting a gas stream comprising methane with a catalyst comprising molybdenum and zinc wherein the catalyst was prepared by contacting a molybdenum oxalate and a zinc compound with a zeolite-containing support.

21. A process as claimed in claim 20 wherein zinc was added to the catalyst as zinc oxalate.

22. A process as claimed in claim 20 wherein the gas stream comprising methane has a methane concentration of from 75 to 100 volume percent.

23. A process as claimed in claim 20 wherein the gas stream comprising methane is derived from biogas.

24. A process as claimed in claim 20 wherein the gas stream containing methane is stranded natural gas.

* * * * *